(12) United States Patent
Nakamura et al.

(10) Patent No.: US 7,982,864 B2
(45) Date of Patent: Jul. 19, 2011

(54) OPTICAL MEASURING SYSTEM

(75) Inventors: Katsushige Nakamura, Tokyo (JP);
Minoru Nakamura, Tokyo (JP);
Katsuhiro Miura, Tokyo (JP); Masao Doi, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 12/067,751

(22) PCT Filed: Sep. 21, 2006

(86) PCT No.: PCT/JP2006/318751
§ 371 (c)(1),
(2), (4) Date: Apr. 13, 2009

(87) PCT Pub. No.: WO2007/034878
PCT Pub. Date: Mar. 29, 2007

(65) Prior Publication Data
US 2009/0213362 A1    Aug. 27, 2009

(30) Foreign Application Priority Data

Sep. 22, 2005   (JP) ................................. 2005-275677

(51) Int. Cl.
*G01N 21/00*    (2006.01)

(52) U.S. Cl. ............. 356/72; 356/73; 356/300; 356/302

(58) Field of Classification Search .................... 356/72, 356/73, 300, 302
See application file for complete search history.

(56) References Cited

U.S. PATENT DOCUMENTS

| 4,844,617 | A | 7/1989 | Kelderman et al. |
| 6,504,608 | B2 | 1/2003 | Hallmeyer et al. |
| 7,468,834 | B2 * | 12/2008 | Wolleschensky ............. 359/370 |
| 7,623,907 | B2 * | 11/2009 | Takaoka et al. ................. 356/39 |
| 2001/0010592 | A1 | 8/2001 | Nakamura |

FOREIGN PATENT DOCUMENTS

| JP | 11-337812 | 12/1999 |
| JP | 2000-227360 | 8/2000 |
| JP | 2001-289619 | 10/2001 |

(Continued)

OTHER PUBLICATIONS

International Search Report dated Oct. 17, 2006.
Written Opinion of the International Searching Authority dated Oct. 17, 2006.

(Continued)

*Primary Examiner* — Gregory J Toatley
*Assistant Examiner* — Iyabo S Alli
(74) *Attorney, Agent, or Firm* — Edell, Shapiro & Finnan, LLC (57) ABSTRACT

An optical measuring system has a first optical measuring instrument and a second optical measuring instrument. The optical measuring system includes a first optical path to guide a first beam from a measuring region to the first optical measuring instrument, a second optical path to guide a second beam from the measuring region to the second optical measuring instrument, an optical system through which the first and second optical paths extend and in which the first and second optical paths are paraxial, a reflection area to change the direction of the first optical path, the second optical path crossing the reflection area, and a light transmission area arranged at a position where the reflection area and second optical path cross each other, the light transmission area having a higher light transmittance than the reflection area.

15 Claims, 4 Drawing Sheets

FOREIGN PATENT DOCUMENTS

| | | |
|---|---|---|
| JP | 2001-311866 | 11/2001 |
| JP | 2003-509667 | 3/2003 |
| JP | 2004-145372 | 5/2004 |
| JP | 2004157246 | 6/2004 |

OTHER PUBLICATIONS

Australian Office Action dated Aug. 14, 2009.

Japanese Office Action 2005275677, dated Feb. 22, 2011, (3 pages).

* cited by examiner

OPTICAL MEASURING SYSTEM

TECHNICAL FIELD

The present invention relates to an optical measuring system having two optical measuring instruments, and particularly, to an optical measuring system having a spectral optical system and an autofocus function.

BACKGROUND TECHNOLOGY

Melanoma (malignant melanoma) is a superficial tumor occurring on the surface of a human body. It looks like a mole. However, if it is assumed as an ordinary mole and is touched or surgically operated, it metastasizes to the whole body and leads to death. It is known that the melanoma metastasizes even by irradiating it with ultraviolet rays of blue wavelength or shorter. Namely, only diagnosing it has a risk of metastasis. Even now, it is said that such a diagnosis relies on experienced doctors and their instinct. It is strongly desired, therefore, to provide a measuring apparatus capable of objectively diagnosing a skin problem such as melanoma without experienced doctors.

DISCLOSURE OF THE INVENTION

A cancer cell usually involves new blood vessels to suck nutrition from the surroundings. Accordingly, if the presence of new blood cells is detectable by observing a skin surface, cancer such as melanoma can be found in an early stage. The new blood vessels, however, are very fine and are hardly detectable with standard imaging techniques.

It is said that a cancer cell has a specific spectral characteristic so that spectrally measuring a two-dimensional area on a skin surface may detect a cancer cell. Measuring a two-dimensional distribution of spectral characteristics by scanning an object with an optical system needs an autofocus mechanism. Namely, it is necessary to always detect and correct the focal position of an optical system in a spectrometry system. For this, a laser beam is emitted to irradiate a measuring region and a beam splitter branches an optical path in the middle of the optical system, to measure the focal position of the optical system and control the position of the optical system. To achieve a spectral measurement and confirm a measuring region, the branched beams must be made incident to a spectrometry unit or must be observed with a monitor. The beam splitter used attenuates reflected beams that are originally weak, and therefore, causes a problem of necessitating high-sensitivity spectral units and imaging units.

MEANS TO SOLVE THE PROBLEM

In consideration of the above-mentioned problem, the present invention provides an optical measuring system capable of measuring a two-dimensional distribution of spectral characteristics of a measuring region and automatically controlling the focus of an optical system without substantially attenuating the quantity of light from the measuring region. The system is also capable of finding a geometrical distribution in the measuring region in real time.

The present invention provides an optical measuring system capable of simultaneously carrying out geometrical and spectral measurements on the surface of a measuring object with a single optical system without directly touching the measuring object. It is also capable of simultaneously carrying out different measurements without attenuating the quantity of light.

According to a technical aspect of the present invention, there is provided an optical measuring system having a first optical measuring instrument and a second optical measuring instrument. The optical measuring system includes a first optical path to guide a first beam from a measuring region to the first optical measuring instrument, a second optical path to guide a second beam from the measuring region to the second optical measuring instrument, an optical system through which the first and second optical paths extend and in which the first and second optical paths are paraxial, a reflection area to change the direction of the first optical path, the second optical path crossing the reflection area, and a light transmission area arranged at a position where the reflection area and second optical path cross each other, the light transmission area having a higher light transmittance than the reflection area.

The first and second optical paths are separated from each other by the reflection area and light transmission area, and therefore, the light quantity of, in particular, the second optical path does not attenuate. This realizes a high-precision optical measurement.

According to a second technical aspect of the present invention, the optical measuring system further includes a laser optical system to emit a laser beam that has an optical path extending through a specific position on a focal plane of an objective optical system, the first optical measuring instrument being a focal position detector configured to detect an irradiation point of the laser beam in the measuring region, the objective optical system being controlled to move according to the detected irradiation point so that the irradiation point may converge to a predetermined location.

Autofocusing to a measuring region enables the second optical measuring instrument to always optically measure a specific location in the measuring region. The measuring region may be shifted to optically measure each location in a two-dimensional area.

According to a third technical aspect of the present invention, the second optical measuring instrument of the optical measuring system is a spectrometry unit including a spectroscope and a two-dimensional imaging unit, to carry out a spectroscopic measurement on a linearly distributed beam, the second optical path extending through the light transmission area and spectroscope to a light receiving part of the two-dimensional imaging unit.

BEST MODE OF IMPLEMENTING THE PRESENT INVENTION

Figure 1:
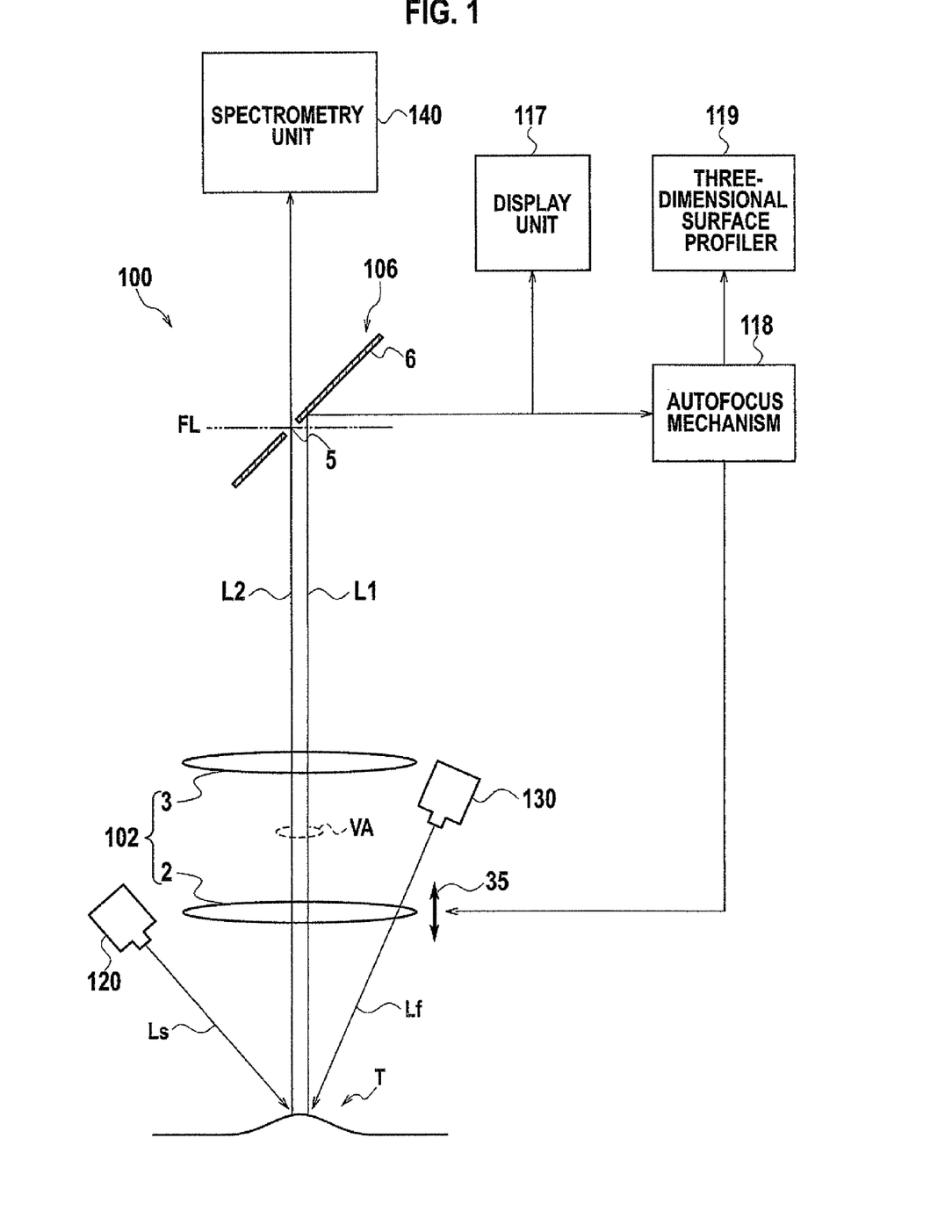
FIG. 1 is a conceptual view illustrating an optical measuring system according to the present invention.

An embodiment of the present invention will be explained with reference to FIG. 1. An optical measuring system 100 according to the embodiment has an autofocus mechanism and includes a main optical system 102 whose focal point is automatically adjustable, a mirror 106 having a slit 5 serving as a light transmission area at the focal position FL of the main optical system, a two-dimensional imaging unit 117, the autofocus mechanism 118, and a spectrometry unit 140 to spectrally separate a beam transmitted through the slit 5 of the mirror 106. In addition, the optical measuring system 100 includes a laser optical system 130 to condense a laser beam Lf to a point on the surface of a measuring object region T in order to adjust the focal position of the main optical system and an illuminating optical system 120 to illuminate the measuring object region.

The spot beam Lf emitted from the laser optical system 130 is a light beam that is thin and can substantially be treated as a ray. The spot beam is scattered at a point on the surface of the measuring object region T, is passed through the main optical system 102 whose focal position is adjustable, is reflected by the mirror 106, and is made incident to the autofocus mechanism 118 having a focal position detector 18.

As will be explained later, the optical measuring system 100 according to the embodiment is an optical path separating system that separates a light beam into a first optical path L1 extending from the measuring object T to a first optical measuring instrument (117 to 119) and a second optical path L2 extending from the measuring object T to a second optical measuring instrument 140.

More concrete embodiments of the present invention will be explained in detail.

<Autofocus Mechanism>

Figure 2:
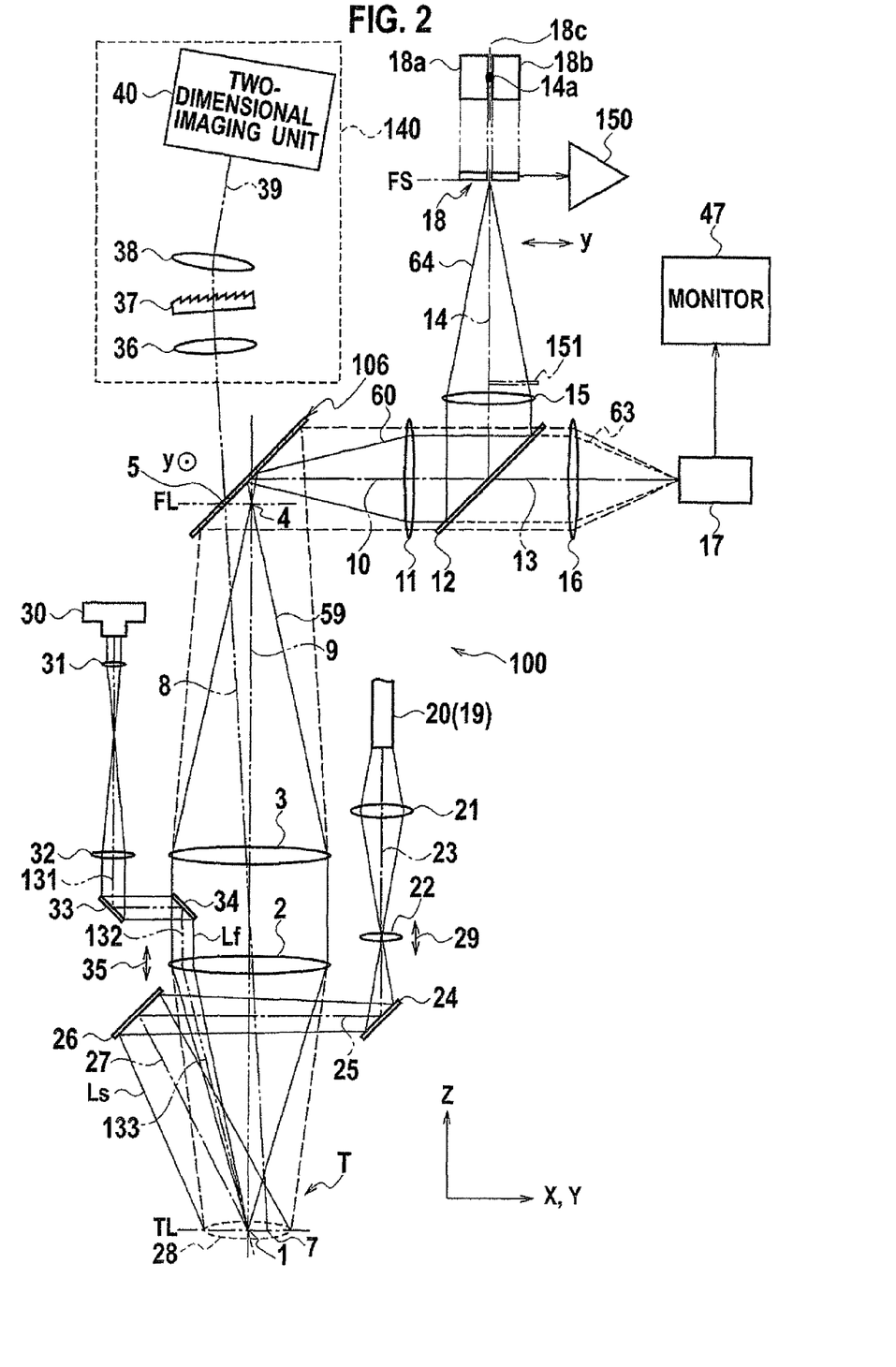
FIG. 2 is a schematic view illustrating the details of the optical measuring system according to the present invention.

The main optical system 102 includes, as illustrated in FIG. 2, an objective optical system 2 and an imaging optical system 3. A light beam emitted from a virtual light source positioned at an anterior focal point TL of the objective optical system 2 partly becomes a parallel beam between the objective optical system 2 and the imaging optical system 3 and forms an image at the focal position FL of the imaging optical system 3. As will be explained later, the objective optical system 2 is movable in a direction 35 that is in parallel to an optical axis L1 (9), to form a focal point on the surface of the measuring object region T.

The laser optical system 130 includes a semiconductor laser oscillator 30, optical systems 31 and 32, and mirrors 33 and 34. A laser beam emitted from the semiconductor laser oscillator 30 has wavelengths of, for example, 635 nm, 670 nm, 730 nm, 820 nm, and 830 nm in a case where wavelengths shorter than a blue color are unusable. The laser beam emitted from the semiconductor laser oscillator 30 is passed through the optical systems 31 and 32 along an optical axis 131, to form a high-precision parallel beam. The mirrors 33 and 34 make an optical axis 132 parallel to the optical axis 9 of the objective optical system 2, to guide the parallel beam to a peripheral part of the objective optical system 2 out of the optical axis 9. The laser beam is a spot beam that is very narrow relative to the objective optical system 2, and therefore, can substantially be treated as a ray. Even if the objective optical system 2 is moved in the direction 35 parallel to the optical axis 9 to adjust the focal point thereof, the laser beam advances along an optical axis 133 and always condenses at a point 1 on the optical axis 9, the point 1 being on a focal plane TL of the objective optical system 2 and positionally fixed to the objective optical system 2. Accordingly, when the focal point is adjusted, the point 1 is positioned on the surface of the measuring object region T.

In the drawing, an X-axis and a Y-axis are fixed in parallel with the surface of the measuring object region T, the X-axis is parallel to the drawing surface and the Y-axis is orthogonal to the drawing surface. An optical path of the laser beam Lf is in a Y-Z plane that is orthogonal to the drawing surface but it is depicted as parallel to the drawing surface for the convenience of explanation. It is not always necessary to set the surface of the measuring object region T horizontally. For example, it may be set vertically.

The laser optical system 130 may be configured so mat the laser beam is condensed to the point 1 by bypassing the objective optical system 2. In this case, the laser optical system 130 is positionally fixed to the objective optical system 2 and is linked with the movement 35 of the objective optical system.

Several percents of the laser beam scattered at the point on the surface of the measuring object region T such as the skin is reflected toward the objective optical system 2, which provides a parallel beam. The parallel beam is passed through the imaging optical system 3 to form an image at a point 4 in the focal plane FL on the optical axis 9 (optical path L1). The imaging point 4 is in the vicinity of a mirror 6. The beam 60 from the focal position FL is reflected by the mirror 6 (hereinafter referred to as slit mirror 106) having a slit or a light transmission area 5 equivalent to the slit into the direction of an optical axis 10 toward a collimator lens 11 that provides a parallel beam.

A dichroic mirror 12 separates only the laser beam into the direction of an optical axis 14 toward an imaging lens 15, which receives the beam 64 and forms an image on a focal plane FS. At the image forming position, there is arranged a position sensor 18 serving as the focal position sensor of the autofocus mechanism 118. The position sensor is a two-piece image sensor 18 (18a and 18b). In a state that the focal position of the objective optical system 2 is adjusted, a laser beam 14a scattered at the focal position of the objective optical system 2 is at an intermediate position 18c between a first light sensing element 18a and a second light sensing element 18b of the image sensor those are arranged adjacent to each other. In connection with the optical path 14 of the laser beam shown in FIGS. 2 and 5, a y-axis direction corresponding to the Y-axis direction fixed to the measuring object region T is orthogonal to the drawing surface. It is depicted, however, in parallel to the drawing surface for the convenience of explanation.

In an off-focus state, the laser beam is scattered on the measuring object region T at a position upper or lower than the focal position 1 on the optical axis 9 of the objective optical system 2. Accordingly, an optical weighted center of the laser beam at the imaging point slants toward one of the first and second light sensing elements 18a and 18b (in the y-direction corresponding to the Y-direction), to form a blurred spot. The objective optical system 2 is controlled so that the laser beam is positioned at the intermediate position 18c, to realize autofocus.

Namely, according to a signal detected by the two-piece image sensor 18, the autofocus mechanism 118 detects a deviation $v_y$ in the y-direction from the intermediate position 18c in the optical weighted center of the laser beam at the imaging point. The deviation $v_y$ corresponds to a deviation of an intersection of the optical axis 133 of the laser beam Lf and the surface 28 of the measuring object region T from the point 1. Namely, the deviation represents a shift of the focal position of the objective optical system 2 from the measuring object surface 28 in the direction of the optical axis 9. A controller 150 of the autofocus mechanism 118 carries out feedback control to zero the deviation $v_y$ by moving the position of the objective optical system 2 in the direction 35 (Z-axis direction), so that the focal position TL of the objective optical system 2 always positions on the measuring object surface 28.

In this way, the position or Z-direction shift of the objective optical system 2 can be used to detect the position (height) of an intersection of the measuring object surface 28 and the optical axis 9. Moving the optical measuring system 100 in the X-direction relative to the measuring object surface 28 results in precisely measuring a distribution of heights in the X-direction of the measuring object surface 28 such as the skin. The laser beam Lf is always scattered at the point 1 on the optical axis 9, and therefore, the autofocus control and three-dimensional surface measurement can be carried out without the influence of the inclination and brightness of the measuring object surface 28. According to the embodiment, the laser beam Lf is condensed by the objective optical system 2, to make the size of the beam at the point 1 into a spot of about several micrometers to several tens of micrometers. This greatly increases a positional resolution and enables a measurement of very fine shape of, for example, new blood vessels.

Between the imaging lens 15 and the two-piece image sensor 18, it is possible to arrange a diaphragm 151 that is offset in an arranging direction (y-direction) of the first and second light sensing elements 18a and 18b. The diaphragm prevents a malfunction when the objective optical system 2 has a high magnification power to cause a large off-focus deviation. The diaphragm 151 may be movable to change the offset.

<Slit Mirror>

Figure 3:
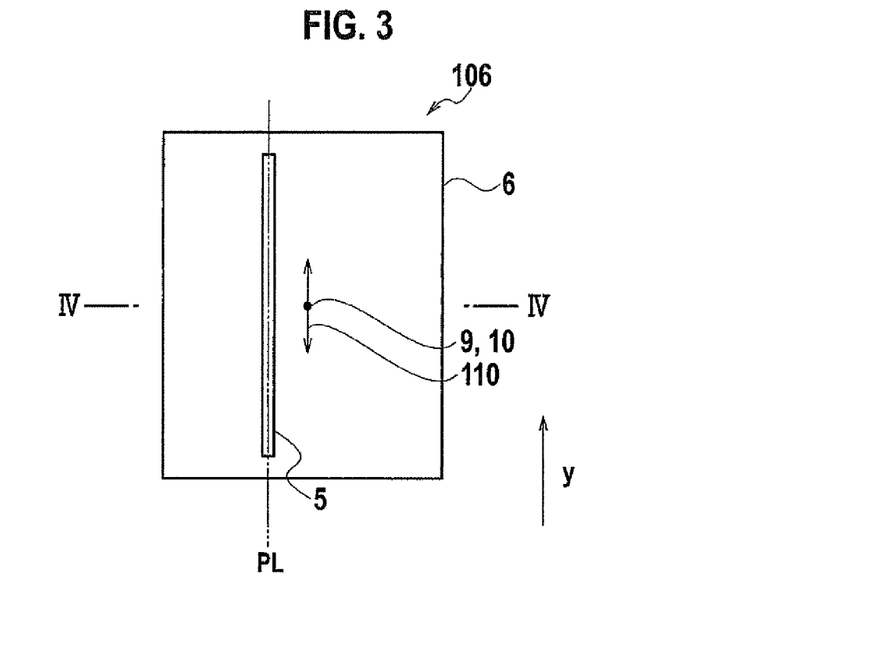
FIG. 3 is a front view mustering a slit mirror according to an embodiment of the present invention.

As illustrated in FIG. 3, the slit mirror 106 of the optical measuring system 100 according to the present invention has the light transmission area 5 in a part of a mirror face (reflection area) 6. The light transmission area 5 is formed to transmit only a beam 58 that advances from a measuring region 7 of the spectrometry unit 140 along the optical axis 8 and typically has an elongate shape such as a rectangular slit-like shape.

Figure 4:
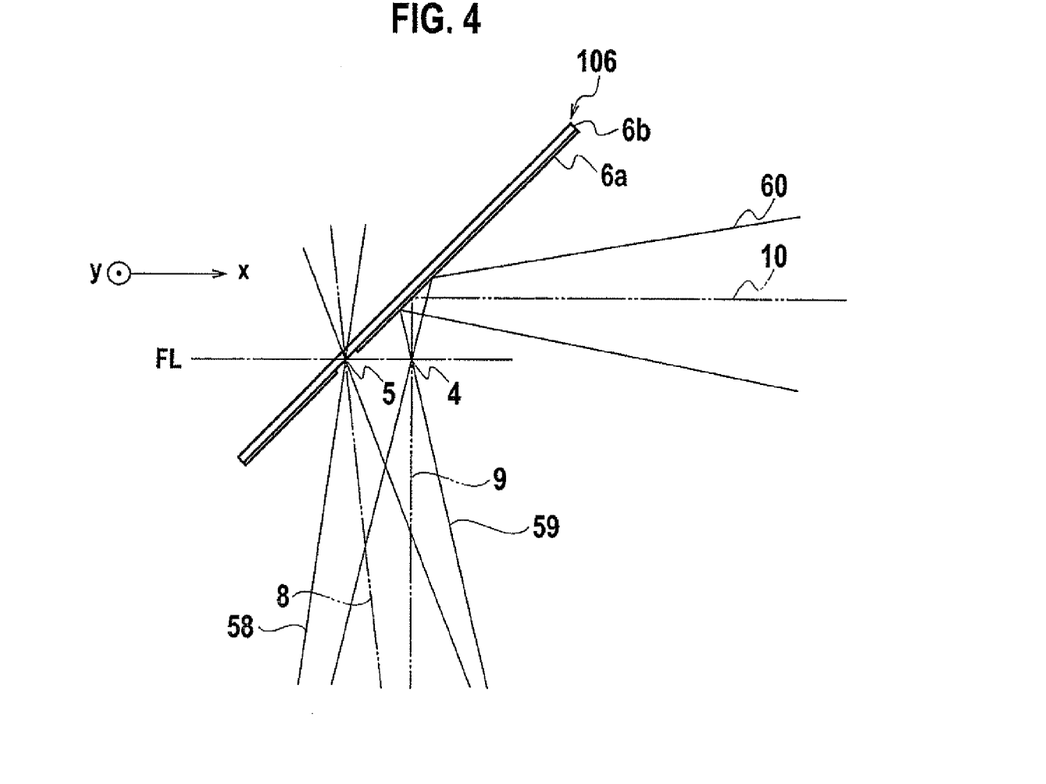
FIG. 4 is a view taken along a line IV-IV of FIG. 3.

The slit mirror 106 as illustrated in FIG. 4 has no slit but is provided with a reflective coat 6a on one face of an optically transparent flat substrate 6b excluding the light transmission area 5. The optical path L1 (optical axis 9) of the laser beam for autofocus is bent by the reflective face 6 of the slit mirror 106 into the direction of the optical axis 10, and the beam 58 for spectrometry selectively passes through the light transmission area 5 of the slit mirror 106 along the optical path L2 (optical axis 8) and is made incident to the spectrometry unit 140. Namely, the slit mirror 106 is arranged so that the reflection area 6 changes the first optical path L1 for guiding the beam from the measuring object region T into the optical axis 10, and at the same time, the light transmission area 5 passes the second optical path L2 (8) for guiding the beam from the measuring region 7 across the slit mirror 106. Between the measuring region 28 and the slit mirror 106, the first optical path L1 (optical axis 9) and second optical path L2 (optical axis 8) are paraxial VA, and therefore, the first optical path (optical axes 9 and 10) never crosses the light transmission area 5 but is bent at a location close to the light transmission area 5. The beam from the measuring object region T excluding the spectrometry region 7 does not reach the light transmission area 5 of the slit mirror 106 and is always reflected by the reflection area 6. The beam from a point in the spectrometry region 7 always reaches the light transmission area 5 of the slit mirror 106 and passes through the same to the spectrometry unit 140.

The light transmission area 5 is configured to be substantially in the focal plane FL of the imaging optical system 3. Namely, a longitudinal main axis PL of the light transmission area 5 is arranged close to the focal plane FL. As a result, a beam reflected by the measuring object region T forms a real image in the focal plane FL due to the imaging optical system 3. Accordingly, the second optical path L2 for spectrometry extending through the light transmission area 5 can be separated from the laser beam (first optical path L1) for autofocus or other beams from the measuring object region T excluding the spectrometry region 7. This is because the laser beam Lf for autofocus is at the point 1 on the optical axis 9 on the measuring object surface 28, the spectrometry region 7 is in the vicinity of the point 1 on the optical axis 9 without overlapping the same, and the light transmission area 5 is substantially in the focal plane FL. The optical axis 133 of the laser beam Lf is inclined relative to the optical axis 9 in an X-Z plane. Accordingly, during an autofocus control operation, the laser beam L1 reflected by the measuring object region T fluctuates in the Y-axis direction around the optical axis 9. Due to this, a reflection point on the slit mirror 106 fluctuates about a specific position in the y-axis direction 110 corresponding to the Y-axis direction. The laser beam L1 fluctuates in parallel to the longitudinal direction of the light transmission area 5, and therefore, never crosses the light transmission area 5, to always achieve stable autofocus control.

A beam splitter (half mirror) is unable to separate beams related to different points in a measuring object region from each other, and therefore, attenuates the light quantity of a branched beam. Contrary to this, the slit mirror 106 according to the present invention can separate two beams related to the spectrometry region 7 and measuring object region T from each other, and therefore, causes no attenuation in the light quantity of each beam. A dichroic mirror may selectively separate a specific spectrum from a beam. This, however, changes spectral components of the beam and separates a given spectral component, and therefore, is functionally different from the slit mirror of the present invention. In practice, it is difficult for the dichroic mirror to completely reflect or transmit a given spectral component. The slit mirror 106 of the present invention can separate a beam related to a specific region without changing spectral components and can block (reflect) a beam related to the other spatial region. Accordingly, the slit mirror 106 is a separating element of an optical path that is appropriate for, in particular, accurate spectrometry.

The width of the light transmission area 5 can be set according to a target region to be instantaneously measured by the spectrometry unit. As will be explained later, a two-dimensional monitor 47 can be used to monitor the measuring object region T, the irradiating point 1 of the laser beam Lf for autofocus, and in addition, the shape of the light transmission area 5. This enables the size and position of the spectrometry object region 7 in the measuring object surface 28 to be confirmed easily. Namely, the beam 58 for spectrometry is separated from the beam 59 by the slit mirror, and therefore, the beam 58 is not included in the beam 60 of the optical axis 10. In other words, the measuring object 7 is observable on a monitor 17 as a real "shadow" of the light transmission area 5.

The optical measuring system 100 according to the present embodiment typically moves the measuring object region T in the X-axis direction, to carry out two-dimensional spectrometry. It is possible to simultaneously monitor the measuring object region T, spectrometry region 7, and laser beam position 1 in real time. Since the system carries out the autofocus operation, the system can simultaneously measure a three-dimensional surface shape. The shape of the light transmission area 5 can optionally be set according to a measuring area of the spectrometry unit 140 and can be composed of a plurality of separate sections.

The light transmission area 5 is sufficient if it has a higher light transmittance than the reflection area. It may be made of a coat having wavelength selectivity. The slit mirror 106 is easily replaceable depending on an object of optical measurement.

<Two-Dimensional Monitor>

Figure 5:
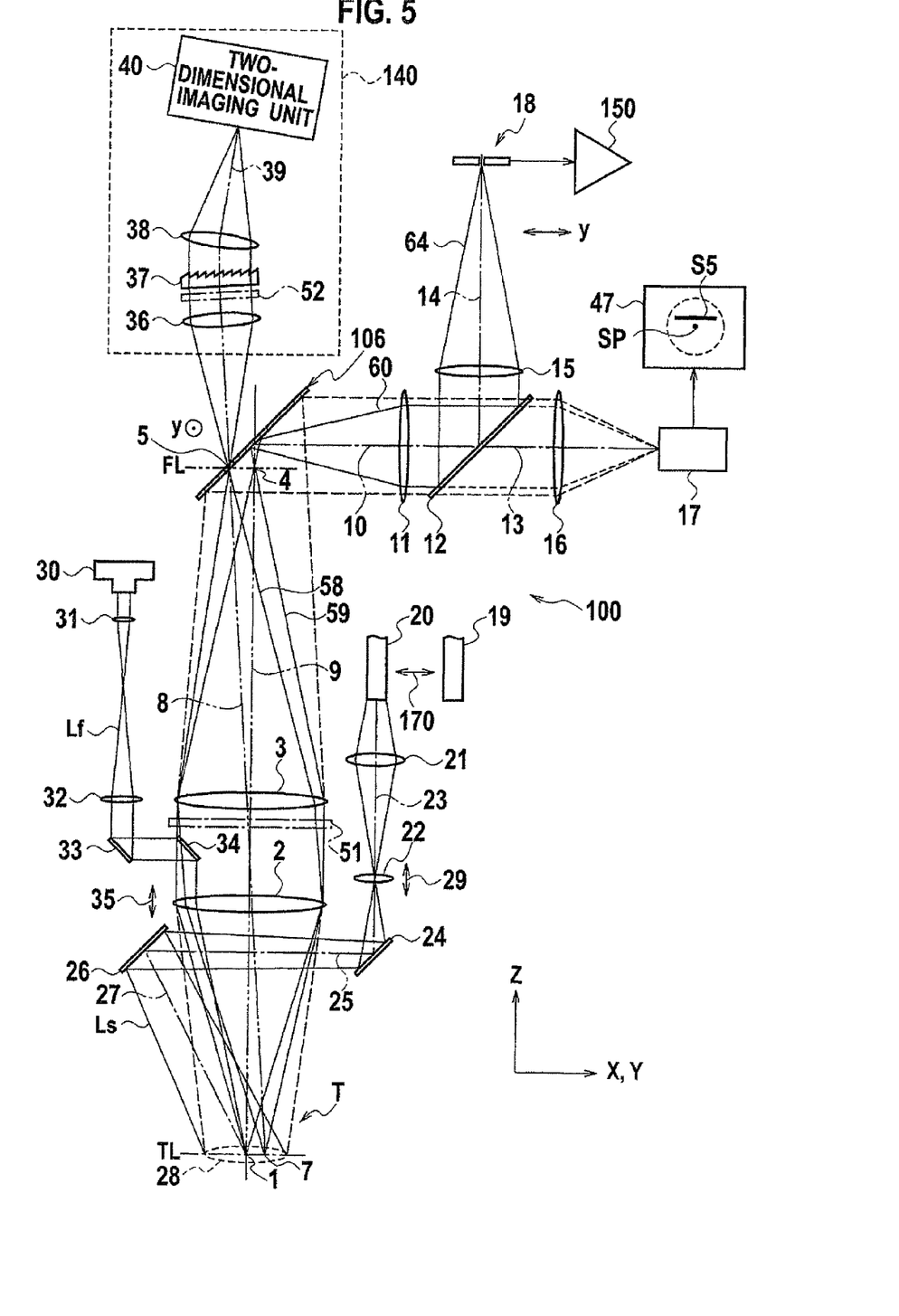
FIG. 5 is a general schematic view illustrating the optical measuring system according to the present invention.

As illustrated in FIG. 5, the display unit 117 includes the two-dimensional imaging unit 17 and a monitor 47, to display the surface of the measuring object region T. A beam passes through the dichroic mirror 12 and is imaged through an imaging lens 16 on a light receiving face of the two-dimensional imaging unit 17. The laser beam for autofocus is mostly reflected by the dichroic mirror 12 due to its wavelength characteristic and slightly leaks. The leaked and transmitted beam 63 forms a weak red spot on a two-dimensional imaging element such as a CCD image sensor. Namely, the laser beam Lf scattered at the point 1 on the focal plane TL of the measuring object surface 28 once forms an image at the focal position 4 of the main optical systems 2 and 3 and again forms an image on the light receiving face of the two-dimensional imaging unit due to the collimator lens 11 and imaging lens 16, to thereby form the spot SP that is observable on the monitor 47.

In the slit mirror 106, the light transmission area 5 is positioned so that the longitudinal main axis PL of the light transmission area 5 is contained in the focal plane 4 of the imaging lens 3. Due to this, the light transmission area 5 can form an image through the two-dimensional imaging unit and can be seen on the monitor. Namely, the part of the measuring object region T that is spectrally measured through the light transmission area 5 can visually be confirmed in real time by looking at a real image of the window (edges) of the light transmission area.

The two-dimensional imaging unit can detect, with a single two-dimensional imaging element, a two-dimensional image of the measuring object whose focus is automatically adjusted, the laser beam, and the light transmission area 5. It is possible, therefore, to easily and correctly confirm the position of the laser beam and the position of the light transmission area 5 that is an object of spectrometry.

The focal length of the imaging lens 3 corresponds to a measuring range. The longer the focal length, the wider the measuring object region T. A ratio of the focal lengths of the objective optical system 2 and imaging lens 3 determines a magnification power. The position of the slit mirror 106 may be fixed and a zooming optical system may be incorporated in the main optical system, to increase the magnification power and improve a resolution of spectral characteristic such as spectrum distribution to provide. Lowering the magnification power results in expanding the measuring range.

<Spectral Analysis with Spectral Optical System>

As shown in FIG. 5, the beam (optical axis 8) transmitted through the light transmission area 5 of the slit mirror 106 is spectrally measured by the spectrometry unit 140. The spectrometry unit 140 according to the embodiment includes spectroscopes 36 to 38 and a high-sensitivity two-dimensional imaging unit 40. The beam transmitted through the light transmission area 5 is passed through the collimator lens 36 to from a parallel beam. The parallel beam is spectrally separated by the transmissive grating 37. Namely, the spectral separation is carried out for the specific measuring region 7 that is linearly distributed (in the Y-axis direction) in the measuring object region T. Spectral components at each point in the specific measuring region 7 distribute linearly. Accordingly, the imaging lens 38 forms a two-dimensional resultant image of spectral components on a light receiving face of the high-sensitivity two-dimensional imaging unit such as HARP imaging tube (trademark).

As explained above, the light transmission area 5 is configured to contain a real image of the linear spectrometry region 7 formed on the focal plane FL. To separate the beam 58 for spectrometry from the laser beam 59 for autofocus at the slit mirror 106, the optical axes 8 and 9 disagree with each other. Namely, the specific measuring region 7 to be measured through the tight transmission area 5 does not overlap the region 1, and therefore, the real image S5 of the "window" of the light transmission area 5 corresponding to the specific measuring region 7 and the real image SP of the region 1 coexist close to each other in the view field of the two-dimensional monitor.

If the measuring object region T is fixed, the spectrometry unit 140 can spectrally measure the linear region 7 of the surface T corresponding to the light transmission area 5 and the measuring region of the spectrometry unit 140. If the optical measuring system 100 scans the surface of a measuring object such as the skin in the X-axis direction, a spectral measurement is carried out over a region defined by a Y-direction scan width and an X-direction scan length.

The length and width of the light transmission area 5 are determined according to the resolution, size, and the like of a two-dimensional image sensor of the high-sensitivity two-dimensional imaging unit 40. Namely, the beam transmitted through the light transmission area 5 is passed through the spectroscopes and is made incident to the high-sensitivity two-dimensional imaging unit, and therefore, the shape of the light transmission area 5 is related to the shape and the like of the image sensor of the high-sensitivity two-dimensional imaging unit. In a case where a HARP imaging tube is employed as the two-dimensional image sensor, the length of a scan line corresponds to the length of the light transmission area 5 and the number and intervals of scan lines are related to the width of the light transmission area. In another case where a two-dimensional solid-state imaging element such as a CCD image sensor is employed as the two-dimensional image sensor, the size of an imaging plane corresponds to the length of the light transmission area 5 and a scan width (Y-axis direction) on the measuring object region T and the size and intervals of pixels are related to a resolution in the scan width direction or a resolution in the width of the light transmission area 5 and a scan direction (X-axis direction). The image sensor of the high-sensitivity two-dimensional imaging unit and the shape and the like of the light transmission area 5 can be related to each other by adjusting the focal lengths of the collimator lens 36 and imaging lens 38.

If the longitudinal direction PL of the light transmission area 5 is set to be parallel to the Y-axis direction, the optical measuring system 100 will be moved for scanning in an orthogonal direction, for example, the X-axis direction. It is preferable that the direction of a scan line of the imaging tube agrees with the longitudinal direction PL of the light transmission area. It is preferable that a pixel arranging direction of the solid-state imaging element agrees with the longitudinal direction PL of the light transmission area. According to the embodiment mentioned above, the grating 37 is transmissive. It is naturally possible to employ a reflective grating.

To further improve the spectral separation ability, polarization filters 51 and 52 may be arranged in the parallel beam of the objective optical system 2 and the parallel beam of the collimator lens 36 before the grating 37. The grating 37 may be any one of transmissive type and reflective type.

<Illuminating Optical System>

The illuminating optical system 120 illuminates the surface and periphery of the measuring object region T. A light source thereof may be selected depending on an object. For example, to excite a photosensitive material talaporfin sodium, an excitation laser (664 nm) 20 is usable. To carry out a three-dimensional measurement or spectral analysis of the surface and periphery of the measuring object T such as the skin, a halogen light source 19 or a white-color LED 19 may be used.

A condenser lens 21 receives a beam of fiber output diameter and forms an image in the vicinity of a relay lens 22. The relay lens 22 enlarges the beam made incident to the condenser lens 21 and illuminates the surface 28 of the measuring object region T. Namely, two mirrors 24 and 26 are arranged so that an optical path Ls may extend along optical axes 23, 25, and 27. If the relay lens 22 is moved in a direction 29 toward the condenser lens 21, the region 28 will be enlarged. If the same is moved away from the condenser lens 21, the region 28 will be reduced. By moving only the relay lens 22, the illumination area can be changed depending on an object. The mirrors 24 and 26 may be flat mirrors or cylindrical mirrors having convex or concave faces.

The illuminating optical system 120 must be configured so that illuminating light may not directly enter the objective optical system 2 and may not produce internal or surface reflections in the objective optical system 2. According to the embodiment, the optical path Ls (optical axes 23, 25, and 27) of the illuminating optical system 120 is arranged to bypass the objective optical system 2. Since a beam from the illuminating optical system 120 does not pass through the inside of the objective optical system, no ghost occurs and no influence is given to spectral analysis or autofocus mechanism.

The objective optical system 2 has a focal length of about 20 to 40 mm that is close to the measuring object surface 28, and therefore, the illuminating optical system 120 may include a plurality of LEDs that surround the objective optical system 2 and directly illuminate the measuring object surface 28.

<Application to PDD Diagnosis and PDT Treatment>

The optical measuring system 100 of the present invention is applicable to early diagnosis and treatment of superficial tumors such as melanoma. A photodynamic diagnosis (hereinafter referred to as PDD) is drawing attention as a diagnostic technique of cancers such as superficial tumors. A tumor tissue or a new blood vessel has a singular spectral characteristic. Based on this, a diagnosis that irradiates the measuring object region T with a beam is useful to find an unclear contour of a tumor or a tumor recurrence. For example, the illuminating optical system 120 may use the halogen light source 19 or white LED 19 to irradiate the measuring object region T with a halogen beam Ls. With an autofocus operation, the spectrometry unit 140 carries out a spectral analysis and the specific object region 7 is scanned in the X-axis direction. Then, it is possible to examine the presence and state of a tumor on the high-sensitivity two-dimensional imaging unit 40. In association with the autofocus operation, the same region is simultaneously measurable for a three-dimensional surface shape. This allows an immediate inspection of fine surface shapes specific to, for example, new blood vessels. To carry out PDD on a superficial tumor such as melanoma, metastasis must be avoided. For this, the wavelength of the laser beam Lf for autofocus must avoid a blue-color wavelength and must preferably be, for example, 635 nm.

If the presence of a tumor tissue is confirmed, a distribution of tumor cells will be identified. Then, the system can be used for a photodynamic treatment (hereinafter referred to as PDT). A specific photosensitive material gathers at a singular location where a tumor tissue or a new blood vessel is present. Based on this nature, the system irradiates the measuring object region T with a beam to annihilate the malignant cells.

For example, the photosensitive material is talaporfin sodium and the illuminating optical system 120 employs a light source switching mechanism 170 to use the laser source 20 of 664 nm and irradiates the measuring object region T with the laser beam Ls. The talaporfin sodium is singularly taken into the tumor such as melanoma and is excited with the laser beam of 664 nm, to generate active oxygen that blocks cellular respiration and annihilates the malignant cells. In a measuring object region such as a skin surface region diagnosed by PDD, a section where tumor cells are distributed can be scanned and treated by PDT.

The monitor 47 can be used to check the state of PDT. If PDT blocks new blood vessels related to the tumor cells and kills them, an absorption characteristic around 664 nm disappears. Accordingly, it is possible to confirm the effect of the treatment by spectral measurement.

The optical measuring system of the present invention can perform PDD to objectively diagnose the presence and distribution of a superficial tumor such as a skin tumor without veteran doctor's experience and instinct. In addition, the system of the present invention can carry out PDT on the spot, if required. The optical measuring system of the present invention is applicable not only to PDD of cancers but also to PDD of other illnesses because the system of the present invention can also perform a spectral diagnosis with the use of the spectrometry unit.

EFFECT OF THE INVENTION

As mentioned above, the embodiment of the present invention can separate the first optical path L1 extending from the measuring region T to the first optical measuring instrument 118 from the second optical path L2 extending from the measuring region to the second optical measuring instrument 140 by the slit mirror 106 without attenuating the quantity of light, to realize high-precision optical measurements. Compared with a related art of the same precision, the present invention can employ inexpensive optical measuring instruments.

Auto-focusing to a measuring region makes the spectrometry unit 140 optically measure a specific location in the measuring region. The measuring region may be shifted to optically measure each location in a two-dimensional area.

The embodiment of the present invention explained above spectrally measures the surface of a human body. The measuring object of the present invention is not limited to the surface of a human body. The present invention is applicable to spectrally measure the surface of a material.

To early diagnose cancer such as melanoma, the excitation laser 20 may excite a photosensitive material such as talaporfin sodium while a skin surface is being scanned and is being observed with the monitor 47. This enables real-time observation and diagnosis of skin illness. In this case, a suspicious region may be measured in detail with the use of the spectrometry unit 140.

The monitor 47 displays the measuring region, the autofocus beam spot SP, and the projection of the light transmission area 5 of the slit mirror indicative of the spectrometry object region 7. Namely, the measuring object can be checked in real time during the measurement and scanning of the measuring region. At the same time, the surface shape of the measuring region is obtainable.

(U.S. Designation)

In connection with designating the United States, this application claims benefit of priority under 35USC §119(a) to Japanese Patent Applications No. 2005-275677, filed on Sep. 22, 2005, the entire contents of which are incorporated by reference herein.

The invention claimed is:

1. An optical measuring system having a first optical measuring instrument and a second optical measuring instrument, comprising:
    a first optical path to guide a first beam from a measuring region to a detecting part of the first optical measuring instrument and a second optical path to guide a second beam from the measuring region to a detecting part of the second optical measuring instrument;
    an optical system through which the first and second optical paths extend, the first and second optical paths being paraxial;
    a reflection area to change the direction of the first optical path passed through the optical system, the second optical path crossing the reflection area; and
    a light transmission area arranged at a position where the reflection area and second optical path cross each other, the light transmission area having a higher light transmittance than the reflection area and being positioned in the vicinity of a focal plane of the optical system.

2. The optical measuring system according to claim 1, wherein the light transmission area is a slit.

3. The optical measuring system according to claim 1, further comprising:
    an objective optical system included in the optical system and movable in an optical axis direction of the optical system; and
    a laser optical system to emit a laser beam as a spot beam having an optical path extending through a specific position on a focal plane of the objective optical system, wherein
    the first optical measuring instrument includes a focal position detector configured to receive the laser beam guided along the first optical path and detect an irradiation point of the laser beam in the measuring region, and
    the objective optical system is controlled to move according to the detected irradiation point so that the irradiation point may converge to a predetermined position.

4. The optical measuring system according to claim 3, wherein
    the focal position detector includes a first light sensing element and a second light sensing element those are arranged close to each other, to detect an irradiation point of the laser beam in an arranging direction of the first and second light sensing elements.

5. The optical measuring system according to claim 4, further comprising
    a diaphragm configured to block part of the laser beam received by the focus position detector, the diaphragm being offset in the arranging direction of the first and second light sensing elements.

6. The optical measuring system according to claim 3, wherein
    an optical path of the laser beam of the laser optical system is set to pass a position that is away from an optical axis of the objective optical system so that the laser beam is made incident in parallel with the optical axis of the objective optical system.

7. The optical measuring system according to claim 3, wherein
    the laser optical system is positionally fixed to the objective optical system.

8. The optical measuring system according to claim 3, wherein
    a position of the measuring region in the optical axis direction is detected according to a moved distance of the objective optical system at an instance that the optical path of the laser optical system crosses the measuring region.

9. The optical measuring system according to claim 3, wherein
    the optical system includes an imaging optical system between the objective optical system and the reflection area and the light transmission area is arranged on a focal plane of the imaging optical system.

10. The optical measuring system according to claims 3, wherein:
    the second optical measuring instrument is a spectrometry unit including a spectroscope and a two-dimensional imaging unit, to carry out a spectroscopic measurement on a linearly distributed beam: and
    the second optical path extends through the light transmission area and spectroscope to a light receiving part of the two-dimensional imaging unit.

11. The optical measuring system according to claim 10, further comprising
    an illuminating unit configured to illuminate the measuring region so that the spectroscopic measurement is carried out, an optical path of illuminating light from the illuminating unit bypassing the objective optical system.

12. The optical measuring system according to claim 11, wherein
    the illuminating light of the illuminating unit has a wavelength that excites a photosensitive material.

13. The optical measuring system according to claims 3, further comprising
    a two-dimensional imaging unit,
    the first optical path being branched after the reflection area and reaching the two-dimensional imaging unit.

14. The optical measuring system according to claim 13, wherein
    a dichroic mirror is arranged at a position where the first optical path is branched, to separate rays of light having wavelengths other than the wavelength of the laser beam.

15. The optical measuring system according to claim 10, wherein
    a polarizing filter is arranged to cross the beams in the optical system or the beam in the spectroscope.

* * * * *